(12) United States Patent
Ren et al.

(10) Patent No.: US 9,899,117 B2
(45) Date of Patent: Feb. 20, 2018

(54) METALLIC NANOMESH

(71) Applicant: University of Houston System, Houston, TX (US)

(72) Inventors: Zhifeng Ren, Houston, TX (US); Tianyi Sun, Waltham, MA (US); Chuanfei Guo, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 14/298,090

(22) Filed: Jun. 6, 2014

(65) Prior Publication Data

US 2014/0377579 A1    Dec. 25, 2014

Related U.S. Application Data (60) Provisional application No. 61/838,796, filed on Jun. 24, 2013.

(51) Int. Cl.
| | |
|---|---|
| *H01B 5/00* | (2006.01) |
| *H01B 1/02* | (2006.01) |
| *H01B 13/00* | (2006.01) |
| *A61N 1/04* | (2006.01) |
| *B82Y 40/00* | (2011.01) |
| *B82Y 30/00* | (2011.01) |

(52) U.S. Cl.
CPC ............. *H01B 1/02* (2013.01); *A61N 1/0472* (2013.01); *B82Y 30/00* (2013.01); *B82Y 40/00* (2013.01); *G06F 2203/04112* (2013.01); *Y10T 428/12424* (2015.01); *Y10T 428/24331* (2015.01)

(58) Field of Classification Search
None
See application file for complete search history.

(56) References Cited

U.S. PATENT DOCUMENTS

| | | | |
|---|---|---|---|
| 7,666,568 B2 | 2/2010 | Gao et al. | |
| 2002/0167619 A1* | 11/2002 | Bietsch | G03B 21/28 348/739 |
| 2006/0056003 A1* | 3/2006 | Tonar | B60R 1/08 359/265 |
| 2011/0248401 A1 | 10/2011 | Hellstrom et al. | |
| 2012/0097204 A1* | 4/2012 | Yu | B82Y 30/00 136/200 |
| 2012/0107598 A1 | 5/2012 | Zou et al. | |
| 2012/0152295 A1* | 6/2012 | Matus | H01L 35/34 136/200 |

(Continued)

FOREIGN PATENT DOCUMENTS

CN    101835624 A    9/2010

OTHER PUBLICATIONS

Lee et al. Nano Letters, 2008, vol. 8, No. 2, 689-692.*

(Continued)

*Primary Examiner* — Vera Katz
(74) *Attorney, Agent, or Firm* — Conley Rose, P.C.

(57) ABSTRACT

A transparent flexible nanomesh having at least one conductive element and sheet resistance less than 300Ω/□ when stretched to a strain of 200% in at least one direction. The nanomesh is formed by depositing a sacrificial film, depositing, etching, and oxidizing a first metal layer on the film, etching the sacrificial film, depositing a second metal layer, and removing the first metal layer to form a nanomesh on the substrate.

12 Claims, 6 Drawing Sheets

(56) References Cited

U.S. PATENT DOCUMENTS

2012/0217165 A1    8/2012  Feng et al.
2015/0309229 A1*  10/2015  Ren ........................ G02B 5/282
                                                                    359/360

OTHER PUBLICATIONS

PCT/US2014/041277 International Search Report and Written Opinion dated Sep. 26, 2014 (11 p.).
Liu, Cai-Hong, et al., "Silver Nanowire-Based Transparent, Flexible, and Conductive Thin Film," Nanoscale Research Letters, vol. 6, No. 75, 2011 (8 p.).
Xu, Feng, et al., "Highly Conductive and Stretchable Silver Nanowire Conductors," Advanced Materials, vol. 24, pp. 5117-5122, 2012 (6 p.).
Chinese Office Action dated Mar. 1, 2017, for Chinese Application No. 201480041541.7 (6 p.).
English Translation of Chinese Office Action dated Mar. 1, 2017, for Chinese Application No. 201480041541.7 (10 p.).
Lee, Phillip, et al., "Highly Stretchable and Highly Conductive Metal Electrode by Very Long Metal Nanowire Percolation Network," Advanced Materials, Jul. 3, 2012, vol. 24, No. 5, pp. 3326-3332 (7 p.).
European Examination Report dated Jun. 28, 2017, for European Application No. 14816980.8 (5 p.).

* cited by examiner

METALLIC NANOMESH

CROSS-REFERENCE TO RELATED APPLICATIONS

This application claims priority to U.S. Provisional Patent Application No. 61/838,796 filed on Jun. 24, 2013 and titled "Superplastic Transparent Metallic Nanomesh" incorporated herein by reference in its entirety.

STATEMENT REGARDING FEDERALLY SPONSORED RESEARCH OR DEVELOPMENT

This work is supported by the U.S. Department of Energy under award number DE-FG02-13ER46917.

BACKGROUND

Field of the Disclosure

The present disclosure relates to nanomaterials. More specifically, the present disclosure relates to a flexible, transparent nanomesh for conductive coatings.

Background of the Technology

With the rapid development of photo-electronics, there is an increasing demand for improved performance and wider application of flexible transparent electrodes. For example, the market for touch screen and foldable display technologies that rely on flexible transparent electrodes continues to grow. Additionally, epidermal electronics represent an emerging application for electrodes with high flexibility.

Transparent, flexible materials including carbon nanotubes, graphene, and metal nanowires are being investigated to replace transparent conductive electrodes such as tin doped indium oxide or indium-tin-oxide (ITO) films. Carbon nanotube and graphene electrodes present a good transmittance of around 80%, but they have a sheet resistance that is greater than about 100Ω/□ (ohms per square). The resistance of these carbon meshes is too high for many photo-electronic applications. In contrast, metal nanomeshes, usually silver (Ag) may achieve high electrical conductivity and demonstrate transparency comparable to indium-tin-oxide (ITO) films. Generally, metal nanomeshes are fabricated by two processes. First, utilizing any of the well-established/conventional, expensive nanofabrication techniques such as electron beam lithography, focused ion beam milling, and nanoimprint lithography, which enable fine features on a sub-100 nm scale. Alternatively, there is a solvent route that can make metal nanowires, such as the aforementioned Ag, at comparatively lower cost and higher throughput. The nanowires produced thusly have a length of between about 1 µm and about 10 µm, and a diameter between about 50 nm and about 100 nm. These nanowires may be assembled to form a random metal mesh electrode. However, the electrical properties of a metal mesh electrode produced accordingly are comparable to conventional nanofabrication techniques, due in-part to the non-uniformity and high resistance of the contacting junction between metal nanowires. While annealing is effective to decrease the junction resistance, it is not compatible with many organic substrates and therefore not suitable for flexible electronics. In some cases, the use of ultralong nanowires can significantly improve conductivity, but the synthesis is more complicated and, in certain instances, the solution-processed Ag nanowires also yield high surface roughness.

BRIEF SUMMARY OF THE DISCLOSURE

A flexible nanomesh is a continuous metal film with isolated holes. In an exemplary embodiment, the nanomesh formed by depositing a film, depositing a first metal layer on the film, etching the film, oxidizing the first metal film, depositing a second metal layer, and removing the first metal layer to form a nanomesh on the substrate. In some embodiments, the nanomesh is transferred between substrates by a floating method.

Disclosed is a nanomesh that is a sheet of nanowires, comprising at least one conductive element, capable of stretching to 200% in at least one dimension at a sheet resistance less than 300Ω/□. Generally, the at least one conductive element comprises an element chosen from the group consisting of aluminum (Al), copper (Cu), gold (Au), silver (Ag), platinum (Pt), palladium (Pd), and the alloys, and combinations thereof. The nanowires in the nanomesh have a thickness between about 10 nm and about 500 nm, a mesh size between about 0.1 µm and about 10 µm, and line width between about 20 nm and about 200 nm. In some configurations, the sheet comprises a transmittance of at least about 40% in the spectrum between about 200 nm and about 1500 nm.

Embodiments described herein comprise a combination of features, characteristics and/or advantages intended to address various shortcomings associated with certain prior devices, systems, materials, and methods. The foregoing has outlined rather broadly certain features and characteristics in order that the detailed description of exemplary embodiments of the invention that follows may be better understood. The various features and characteristics described above, as well as others, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes disclosed herein. It should also be realized by those skilled in the art that such equivalent constructions do not depart from the spirit and scope of the invention as set forth in the appended claims.

BRIEF DESCRIPTION OF THE DRAWINGS

For a detailed description of the exemplary embodiments of the disclosure, reference will now be made to the accompanying drawings in which.

DETAILED DESCRIPTION OF THE DISCLOSED EMBODIMENTS

Overview: Generally, a flexible transparent metal nanomesh is a continuous metal network on the nanoscale. The metallic network retains high electric conductivity and transparency under large deformations arising from stress or bending. Disclosed herein are a flexible transparent metallic nanomesh and a manufacturing method therefor.

Generally, a disclosed method comprises a metal oxide/oxide bilayer lift-off metallization followed by wedging transfer. The nanomesh is fabricated by a non-lithographic bilayer lift-off metallization process, in which the mask layer originates from a self-assembled metallic indium (In) film. Such method is configurable to permit control and tuning of the nanowire width, mesh size, and thickness of the nanomesh. In some configurations, the metal nanomesh may be supported on silicon substrate to facilitate aqueous floating and intact transfer to another substrate. In certain instances, the substrate may comprise a hydrophobic or hydrophilic substrate, without limitation.

Figure 1:
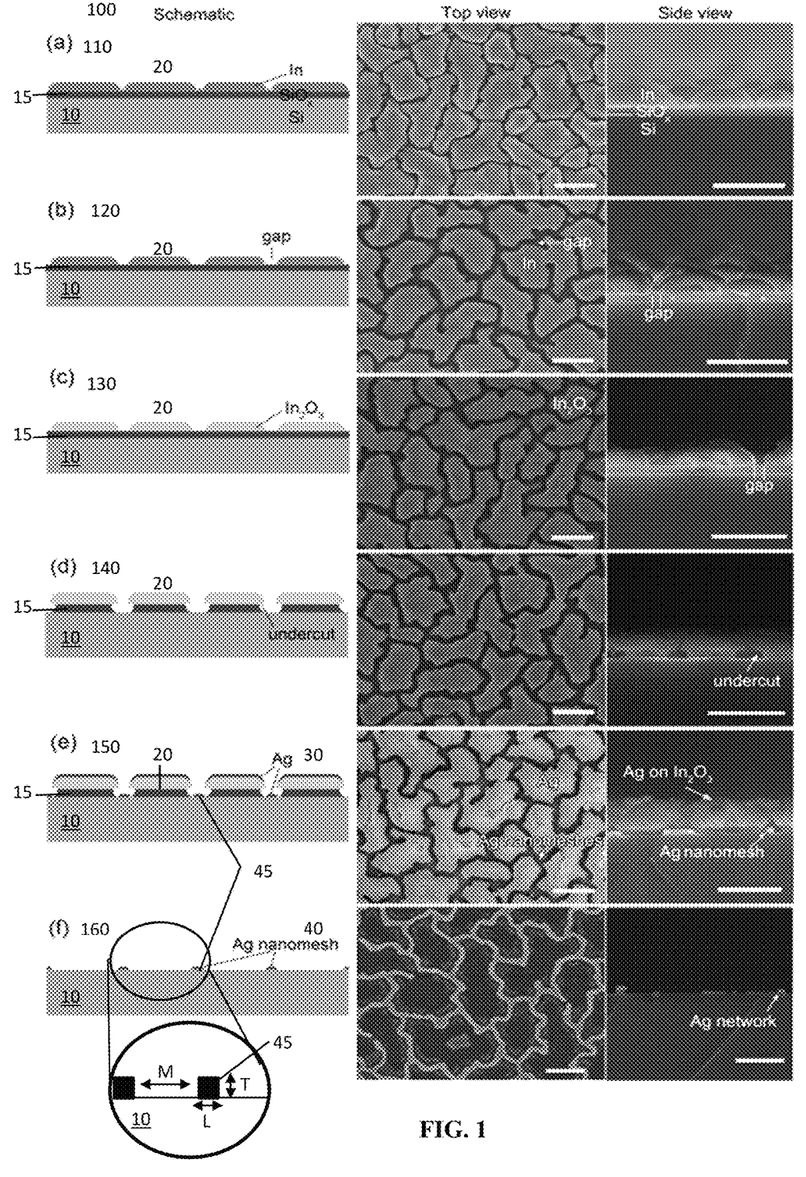
FIG. 1. schematically illustrates the steps involved in the fabrication of metal nanomeshes with corresponding top and cross-sectional SEM views. These steps including (a) depositing a sacrificial film 15, (b) depositing a first metal film 20, (c) etching and (d) oxidizing the metal film, (e) depositing a second metal film 40, and (f) removing the sacrificial film.

Structure: Referring now to FIG. 1 there is illustrated and described herein a metallic nanomesh with a high transmittance and low resistance. In instances, the metal comprises aluminum (Al), copper (Cu), gold (Au), silver (Ag), platinum (Pt), palladium (Pd), and the alloys, and combinations thereof. In exemplary configurations disclosed herein, the metals comprise gold (Au), silver (Ag), platinum (Pt), and the alloys thereof.

In the nanomesh of the various embodiments, the nanowires comprise a thickness or diameter of the wires between about 10 nm and about 500 nm, or alternatively, between about 20 nm and about 200 nm. In certain exemplary configurations, the nanowires have a thickness of between about 50 nm and 100 nm. Further, the nanomesh formed by the nanowires includes holes that have a size or diameter of between about 0.1 μm and about 10 μm; or alternatively, between about 0.2 μm and about 9 μm; and in exemplary configurations, between about 0.4 μm and about 1.0 μm. As used herein, a nanomesh's "mesh size" is defined by the hole or aperture size in the mesh, such that a nanomesh having a mesh size of between about 0.4 μm and about 1.0 μm, for example, means the nanomesh has holes or apertures of that size. Without limitation by theory, the dimensions of the nanomesh may be at least partially determined by the metal of the nanowires.

Further, the nanomesh of the present disclosure is configured for transmittance in the ultraviolet to infrared spectrum, including the visible spectrum. For example, the nanomesh is configured for transmittance between about 200 nm and about 1500 nm, alternatively, between about 300 nm and about 1400 nm, and in exemplary configurations between about 400 nm and about 1000 nm. Generally, the nanomesh is configured for a transmittance of at least about 40%; alternatively a transmittance of at least about 50%, and in exemplary configurations a transmittance of at least about 60% within this spectrum. Further, in some instances, the transmittance is tunable dependent on the metal or semi metal used, the nanowire thickness, and the mesh size, such that in certain applications the transmittance is between about 50% and about 95%, and alternatively between about 60% and about 95%.

The nanomesh of certain embodiments is further configured to have a flexibility based on the ratio of the stretched or strained dimension relative to the initial dimension before the nanomesh is subjected to the stretching or staining Resistance change at strained states is used to characterize the flexibility. Alternatively, the flexibility of the nanomesh may be measured by the percent strain. In general, the nanomesh configured according to the present disclosure comprises a flexibility of at least about 100% strain; alternatively, at least about 125% strain, and in exemplary configurations, at least about 150% strain. Without limitation by theory, in certain configurations, by altering the metal or semi metal used, the nanowire thickness, and the mesh size, a nanomesh formed according to the present disclosure may have a strain of at least about 200%.

The nanomesh of certain embodiments comprises long metal nanowires that are connected with low contact junction resistance. Thus, the nanomesh maintains a high conductivity evidenced by low sheet-resistance, wherein sheet resistance is defined by Ohms per square area ($\Omega/\square$). In instances, the nanomesh of the present disclosure has a sheet resistance that is less than about $30\Omega/\square$; alternatively, less than about $20\Omega/\square$; and in certain configurations the sheet resistance is less than about $10\Omega/\square$. Without limitation by theory, in certain configurations, by altering the metal or semi metal used, the nanowire thickness, and the mesh size, a nanomesh formed according to the present disclosure may have a sheet resistance that is less than about $5\Omega/\square$.

Method: Referring now to FIG. 1, there is illustrated a method 100 for fabricating a nanomesh. Generally, method 100 utilizes the concepts of grain boundary lithography for making semi-metal or metallic nanomeshes. Further, the nanomeshes are transferred in method 100 to a substrate by floatation and contact transfer. More specifically, the method 100 comprises depositing 110 a sacrificial film 15 on a substrate 10, depositing 115 a first metal 20 overlayer, etching 130 the sacrificial film 15, oxidizing 140 the first metal overlayer 20, etching 150 the sacrificial film 15, depositing 160 a second metal 30, and removing 170 the sacrificial film 15. In instances, the nanomesh 40 remains on the substrate 10. The nanomesh 40 comprises a network of connected nanowires 45 having a thickness T, a line width L, and mesh size M.

Figure 2:
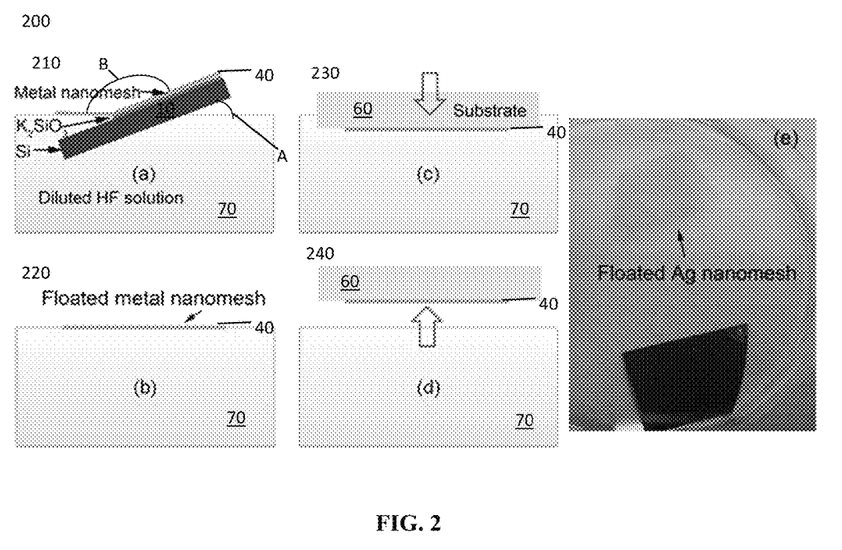
FIG. 2. schematically illustrates transferring of a metal nanomesh 40 to a substrate 60 and a photograph of a floating nanomesh according to one embodiment of the present invention. The process includes (a) and (b) wedging the nanomesh on a solution 70, (c) and (d) contacting and lifting-off the floated nanomesh with targeted substrate 60.

Referring now to FIG. 2, there is illustrated a method 200 for transferring a nanomesh. Generally, the method 200 comprises floating 210 the nanomesh 40 on an aqueous solution 70, stabilizing 220 the nanomesh on the surface of the aqueous solution, contacting 230 the nanomesh 40 with a substrate 60, and lifting 240 the nanomesh 40 off the solution.

Referring again to FIG. 1, the method comprises depositing 110 a sacrificial layer on the substrate. Generally, the substrate 10 itself comprises a non-metal element, for example silicon. In instances, depositing 110 an etchable layer 15 comprises depositing a non-metal, a semi-metallic or metallic element on the substrate. Further, the etchable layer 15 comprises an oxide of the non-metal, semi-metal, or metal element. In exemplary instances, the etchable layer 15 comprises silicon oxide ($SiO_x$). Depositing 110 the sacrificial layer 15 may be done by any method, including but not limited to chemical-vapor-deposition, sputtering, thermal sublimation, and combinations thereof. In exemplary steps, the depositing the sacrificial layer 110 comprises sputtering. In some configurations, the sacrificial layer 15 comprises an oxide layer.

The method 100 comprises depositing 120 a first metal 20 on the etchable layer 15. Without limitation, the first metal 20 is a metal or semi-metal element. Depositing 120 the first metal 20 comprises leaving cracks or gaps 25 in the first metal 20. Without limitation by any particular theory, solid metal forms crystals or grains having ordered layers of metal or semi-metallic atoms. The conditions and rate of deposition, generally determine the grain size of a metal. Thus, it may be understood that the gaps 25 in the first metal 20 are spatially arranged based on and around the perimeter of the first metal grains. The first metal 20 comprises any metal or semi-metal element having a grain size that is size or diameter between about 0.1 µm and about 10 µm; alternatively the grain size is between about 0.2 µm and about 1 µm; and in exemplary configurations between about 0.4 µm and about 0.8 µm. Depositing 120 the first metal 20, further comprises any method of depositing a metal or semi-metal element, including without limitation sputtering, chemical vapor deposition, or electron-beam evaporation.

Etching 130 the film 15 comprises removing the film 15 from the substrate 10. Generally, the first metal 20 acts as a mask after the etching 130 step and subsequent oxiding 140. The gaps 25 that do not cover the sacrificial film 15 permit the removal of the film 15 from the substrate 10. In instances, etching 130 the film comprises washing the film in an ionic and oxidizing solution. Generally, the ionic solution comprises an aqueous ionic solution, for example an acidic solution. In exemplary instances, the aqueous acid solution is selected from those capable of etching or removing a metallic-oxide or semi-metallic oxide from a substrate 10. Further, the aqueous acid solution comprises nitric acid ($HNO_3$) in certain instances. Without limitation by theory, etching 130 the film further comprises controlling the width of the gap 25.

The method 100 comprises the step of oxidizing 140 the overlayer. Generally, the overlayer is the first metal layer 20. Generally, oxidizing 140 the first metal layer 20 comprises exposing the first layer to an oxidant, for example oxygen. In some configurations, oxidizing 140 the first metal layer 20 comprises annealing in air or other oxidant, or altering the temperature. Alternatively, oxidizing 140 the first metal layer 20 comprises washing the deposited layers in an ionic solution, for example an acid. In exemplary instances, oxidizing the first metal layer comprises a combination of washing the first metal layer with an oxidant and thermal oxidation. Without limitation by theory, oxidizing 140 the first metal layer 20 comprises increasing the size of the gaps 25 between metal grains by at least partially degrading the outer layer of metal atoms in each grain. Further, oxidizing 140 the first metal layer 20 comprises forming a mask. Etching sacrificial film 150 comprises of rinsing in etchant, leading to the formation of undercuts. The metal oxide film from the first metal 20 acts as the mask layer to protect the sacrificial layer, whereas the uncovered parts, the gaps 25, are etched. Without limitation by theory, etching 150 the film further comprises undercutting the oxide mask layer transformed from oxidizing 140 the first metal film.

Depositing 160 a second metal 30, comprises depositing the nanowires 45 that form the nanomesh 40. As described hereinabove, depositing 160 a second metal 30 may be achieved by any method and in certain instances, the method comprises electron beam evaporation, or thermal evaporation. In instances, depositing 160 the second metal comprises depositing at least one of the elements of aluminum (Al), copper (Cu), gold (Au), silver (Ag), platinum (Pt), palladium (Pd), and the alloys, and combinations thereof. In exemplary configurations disclosed herein, the metals comprise gold (Au), silver (Ag), and the alloys thereof.

In order to leave the nanowires 45 behind forming the nanomesh 40, removing 170 the second metal comprises removing 170 the mask of the second metal 30 and the sacrificial film 15 thereunder. In instances, removing 160 the second metal 30 comprises washing the nanowires 40 in an aqueous ionic solution. In certain instances, the aqueous ionic solution is capable of dissolving the sacrificial layer 15, such that the first metal 20 that forms the mask and the second metal 30 dissolve or form a suspension. The aqueous ionic solution generally comprises an acid, such as hydrofluoric (HF) acid as described hereinabove. In some configurations of the present method 200, removing 170 the second metal 30 comprises washing the nanowires 40 with a basic solution. In certain configurations, the basic solution comprises potassium hydroxide (KOH).

Referring again to FIG. 2, floating 210 the nanomesh on an aqueous solution comprises wedging the nanomesh 40 into an aqueous ionic solution. More specifically, wedging the nanomesh 40 into an ionic solution comprises inserting the substrate 10 into the aqueous ionic solution at an acute angle A. Thus, angle B with respect to the surface of the substrate supporting the nanomesh 40 is an obtuse angle. The aqueous ionic solution may be any solution disclosed hereinabove, for example an HF acid solution. In further instances, the ionic solution used for floating 210 the nanomesh may be dilute, for example less than about 5% by volume, alternatively, less than about 3% by volume and in certain instances, about 1% by volume. The lower concentration is desired for less pollution problems.

Stabilizing 220 the nanomesh 40 comprises removing the substrate 10 from the solution and verifying that the nanomesh 40 has not physically deformed. In instances, the nanomesh 40 may wrinkle, bend, fold, or partially submerge in the ionic solution. Stabilizing 220 the nanomesh reduces or eliminates the instances of these configurations. Further, stabilizing the nanomesh may comprise altering surface tension of the solution. Without limitation by theory, changing the surface tension of the ionic solution may permit functionalization or other alteration of the surface characteristics of the nanomesh. In some operations, functionalizing the nanomesh comprises inducing a hydrophilic or hydrophobic affinity to the nanomesh surface.

Subsequently, the method 200 comprises contacting 230 the nanomesh with a substrate, and lifting 240 the nanomesh off the solution. Generally, as shown in FIG. 2c, contacting 230 the nanomesh with a substrate comprises using a planar substrate 60 to at least partially submerge the nanomesh 40. The nanomesh 40 remains in contact the planar substrate 60 through hydrostatic pressure. Alternatively, the nanomesh 40 is hydrophilically or hydrophobically associated with the planar substrate 60. The association of the nanomesh 40 with the planar substrate 60 permits the nanomesh to escape the surface tension of the ionic aqueous solution. Alternatively, in some instances, the substrate 60 is not planar, but rather has a complex three dimensional structure, such that a combination of hydrostatic pressure and the hydrophobic or hydrophilic interactions causes the nanomesh 40 to conform to the substrate's three-dimensional shape.

To further illustrate various exemplary embodiments of the present invention, the following examples are provided.

EXAMPLES

Fabrication and transfer of floated Ag nanomeshes: The $SiO_x$ film (65 nm) and In film (about 100 nm) were deposited by using a magnetron sputter, such as the AJA International Inc., ORION-8 magnetron sputtering system, and the Ag films were deposited by using an electron beam evaporation system. The floated metal nanomeshes were made by three steps: (1) rinsing the samples in blended solution of HF (10%) and $H_2O_2$ (0.6%) for 20-40 sec, for example with Ag nanomeshes, or 80 secs, for example for Au nanomeshes, (2) rinsing in 60° C. KOH (2%) solution until the Ag nanomesh goes out and accordingly the sample turns gray, and drying with $N_2$ gas flow, (3) wedging into diluted hydrofluoric acid (HF) (1%) slowly. The metal nanomesh was then transferred to hydrophobic or hydrophilic substrate by slowly pressing the substrate on the floated nanomesh, and after the nanomesh attaching to the substrate it was lifted.

The morphology of the samples was taken by using a scanning electron microscope. Topographic images were taken with an atomic force microscope. Reflectance spectra were recorded with an integrating sphere spectrometer in the wavelength range from 400 to 1000 nm. Sheet resistance was measured by using the van der Pawn method, with four electrodes at four corners of a square of the sample. Stretching experiment was conducted with a home-made setup, and meanwhile the resistance was measured by a two-probe method.

A bilayer lift-off metallization technique offers advantages in resolution, removal, process simplicity, undercut control, and yield over conventional single-layer lift-off process. In this work, the bilayer consists of an $In_2O_3$ mask layer and a $SiO_x$ sacrificial layer for undercut formation. The $In_2O_3$ mask layer is transformed from In film by $HNO_3$ etching and thermal oxidation. The as-deposited In film is made of monolayered In grains, after $HNO_3$ etching a gap is formed with a controllable width between neighboring grains, called islands. FIG. 1(a)-(f) shows six steps involved in the grain boundary lithography: (a) deposition of a 65 nm thick SiOx sacrificial layer on a Si wafer (resistivity: 5-7 Ω·cm, thickness: 0.5 mm), followed by a 100 nm thick In film, (b) etching in 20 wt. % $HNO_3$ for gap formation, (c) thermal oxidation at 400° C. for 2 h to form $In_2O_3$ islands, (d) rinsing in 5 wt. % HF for 12 s, leading to the formation of undercuts, (e) deposition of a about 30 nm Ag or Au film on top of the HF etched surface, so that a metal nanomesh is formed in the gaps, and (f) lift-off process to dissolve the $SiO_x$ and removal of $In_2O_3$ islands in 5% HF solution to form a metal nanomesh on the substrate.

The middle and right columns in FIG. 1 are scanning electron microscopy (SEM) images, showing top view and cross section view, respectively and corresponding to the steps of (a)-(f) described in the preceding paragraph. FIG. 1(a) shows an $In/SiO_x/Si$ structure, in which the In film is made of an monolayer of In grains with an average diameter of 650 nm, with quite narrow grain boundaries. FIG. 1(b) shows the morphology of the film after etching in $HNO_3$ for 16 s. The diluted $HNO_3$ removes all tiny In particles and widens the gaps between large In islands to 60-70 nm, forming an In island film. FIG. 1(c) demonstrates the morphology of the $In_2O_3$ film by thermal oxidation, with $In_2O_3$ islands taking exactly the same morphology of In islands. With a process of rinsing in HF, undercuts are formed as a result of partial removal of $SiO_x$ (FIG. 1(d)). By depositing a metal film with a thickness smaller than that of the $SiO_x$ layer, a metal nanomesh is formed in the grooves. The undercuts can guarantee the formation of metal nanomesh in the grooves, and the configuration of the nanomesh is defined by the gaps (FIG. 1(e)). The last step is a lift-off process under ultra-sonication for tens of seconds, during which $SiO_x$ and $In_2O_3$ islands are removed, leaving a metal nanomesh on the substrate. In the last step, the sample should be well shaken so that liquid flow could take away all $In_2O_3$ islands.

Line width, mesh size, and thickness of the metal nanomesh can be controlled. The line width is defined by the gap resultant from etching of the first metal; in certain instances, it may be considered the thickness of the nanowires. The gap formation in diluted $HNO_3$ involves two processes, the surface oxidation (passivation) of In islands and acidic etching of the oxide skin, expressed as:

$$2In + 2HNO_3 \rightarrow In_2O_3 + 2NO\uparrow + H_2O \qquad (1)$$

$$In_2O_3 + 6H^+ \rightarrow 3H_2O + 2In^{3+} \qquad (2)$$

If the etching process does not involve oxidation, then metallic In will be directly etched by H+. Owing to the fact that etching rates differ for different facets, the gap width will therefore not be homogeneous. And this process will be very fast. Alternatively, an oxide skin could lead to isotropic etching that is similar to the isotropic etching of single crystalline Si wafer in HNA solution (blended solution of HF, $HNO_3$, and $CH_3COOH$, in which $HNO_3$ is the oxidant). The surface oxidation greatly decreases the etching rate to a controllable level. In comparison, 4 mol·L$^{-1}$ HCl solution (a non-oxidizing acid whose concentration of H$^+$ is close to that of the $HNO_3$ solution we used) could dissolve the In film in a very short time, such as one second. Note that the oxide skin is dynamically formed so that there is always an oxide layer on the In islands. The oxidation-acidic etching process makes the gap width quite homogeneous and well controllable.

Figure 5:
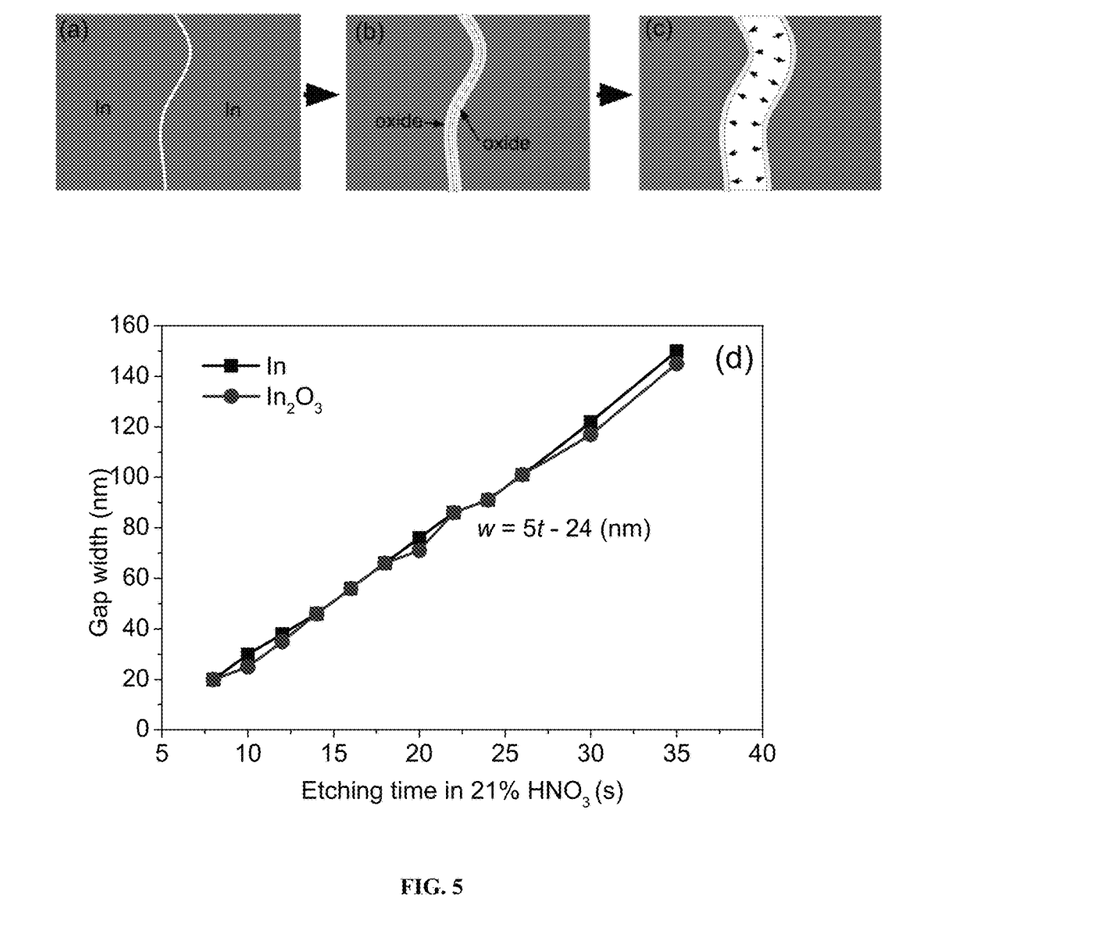
FIG. 5. illustrates schematically (a)-(c) the steps of surface oxidation-acidic etching in diluted $HNO_3$, and (d) dependence of gap width on etching time.

FIG. 5(a)-(c) illustrate the process of etching 130, including surface oxidation (or passivation) and acidic etching. The gap width (w) is shown to increase linearly with the increasing of etching time (t). FIG. 5(d) plots the dependence of gap width on etching time in conditions where, in this case, 20 wt. % $HNO_3$ at room temperature, showing that w is linear to t. After thermal oxidation at 400° C. for hours, the gap width is almost unchanged, due to that the expansion of the islands is confined by the underlying $SiO_x$.

The lateral isotropic etching from a grain boundary offers controllability over the width of nanowires, and the mechanism is much different from main stream nanofabrication techniques. For example, for direct writing techniques including electron beam lithography, focused ion beam milling, and laser direct writing, the feature size of the fabricated metal nanowires is mainly determined by the spot size of energy beam; and for nano-imprinting lithography, size of the template defines the feature size of the fabricated structures. But in the present work, we applied H$^+$ ions to laterally etch the surface-oxidized In islands from the boundary, leading to controllable gaps whose width can be tuned on a molecule scale. Moreover, the etching process of a wafer scale sample can be finished in tens of seconds, quite suitable for mass production.

Apart from the width, mesh size (M), which equals to the size of In islands, is another important parameter. The island size is found to be linear to the thickness (or deposition time) of the In films, with an empirical relationship of M=7h nm, where h is the film thickness (when h is in the range from 50 nm to 500 nm). Besides, the thickness of the metal nanomeshes can also be controlled by varying the metal film thickness. Therefore, line width, mesh size, and thickness of the metal nanomeshes are all well controllable.

In order to completely remove the $In_2O_3$ grains and protect the metal mesh, we use catalytic etching in which the metal nanomesh embeds into Si wafer with a depth of several hundred nanometers, and then the $In_2O_3$ grains are removed in water with a lens paper. Metal nanomeshes on or embedded in silicon wafer, however, are difficult to be directly transferred to other substrates because of the good adhesion of the metal/Si interface. A dissolvable layer inserted in the metal mesh and Si substrate solves this problem. For this reason, we first rinse the sample in hot diluted KOH solution (wt. 2%) to introduce a $K_2SiO_3$ layer, and then slowly wedge the sample into diluted HF solution (wt. 1%) with an incidence angle of about 30° (FIG. 2a). As the $K_2SiO_3$ layer gets dissolved in HF, the metal nanomesh is pushed away from the hydrophobic Si surface, and as a result it floats on the solution (FIG. 2b and e). An optimized route is that before the nanomesh is completely released, we slowly lift the sample and insert the sample again to deionized water to avoid introducing too much HF. It should be noted that after rinsing in KOH, the samples must be dried or else the nanomeshes will not float on water. This is because only dried nanomesh can be pushed away from the wafer by the surface tension of water.

The metal nanomeshes do not sink in water, and they float on water even without any folds or wrinkles Although Ag and Au are hydrophilic, water could not penetrate nanomeshes of Ag or Au because surface tension of water can support the meshes (similarly, even a small paper clip made of metal can float on water). Moreover, a component of surface tension of water pulls normally and horizontally to each nanowire. And at a macro-level, this force is outward and perpendicular to the edges of a nanomesh and therefore keeps the nanomesh unfolded.

Additional Discussion: It has been shown hereinabove that wedging transfer of nanomeshes is viable. A substrate was placed on bottom of a beaker and pumped down water, and a probe was used to control the position of floated structure for alignment. Disadvantages of this method include two aspects: it has to drain water (this is troublesome and is not applicable for light substrates with a density less than that of water); and it is also not applicable to hydrophobic substrates because water will destroy the metal nanomesh. But for flexible photo-electronics, the substrates are often hydrophobic and light organic materials. Even for a hydrophilic substrate, there will also be a water membrane between metal nanomesh and the substrate, and it might lead to the formation of wrinkles or folds during drying (graphene flakes transferred by this method often have wrinkles.) To avoid damage or deformation, the substrate should not contact water, so the substrate must be placed on the metal nanomesh from the air side (FIG. 2c and d). Our experimental results indicating that this simple method is more effective, and it is able to transfer metal nanomeshes onto hydrophobic or hydrophilic substrate (exemplified by PDMS and metal, respectively) without any damage or even deformation. The result indicates that for wedging transfer, introducing water between substrate and floated nanostructures should be avoided.

The Ag and Au nanomesh have excellent electrical conductivity. For a 40 nm thick silver nanomesh with a mesh size of about 700 nm and a line width of about 90 nm processed on a 1 cm×1 cm silicon wafer, the sheet resistance is about $7\Omega/\square$. This is lower than that of carbon nanotube- and graphene-based transparent electrodes, commercial ITO films, and solution processed Ag nanomeshes. The low resistance should be related to the absence of high resistance "junctions", which is a problem for solution-processed Ag nanomeshes. The disclosed Au nanomeshes demonstrate a slightly higher sheet resistance but when optimized $10\Omega/\square$ is achievable, more than one order lower than that of solution processed Au nanomeshes (>400 $6\Omega/\square$). Typically, the Au nanomeshes having a mesh size of 1 μm, thickness of 35 nm, and wire-width of 70 nm demonstrate a sheet resistance of 20-30$\Omega/\square$. It is worth noting that the electrical conductivity of the nanomeshes can be well tuned by simply varying gap widths between $In_2O_3$ islands and/or metal film thickness. For example, Ag nanomesh samples with a thickness of 45 nm, keeping other parameters the same, present an even lower sheet resistance of about $6\Omega/\square$.

Figure 3:
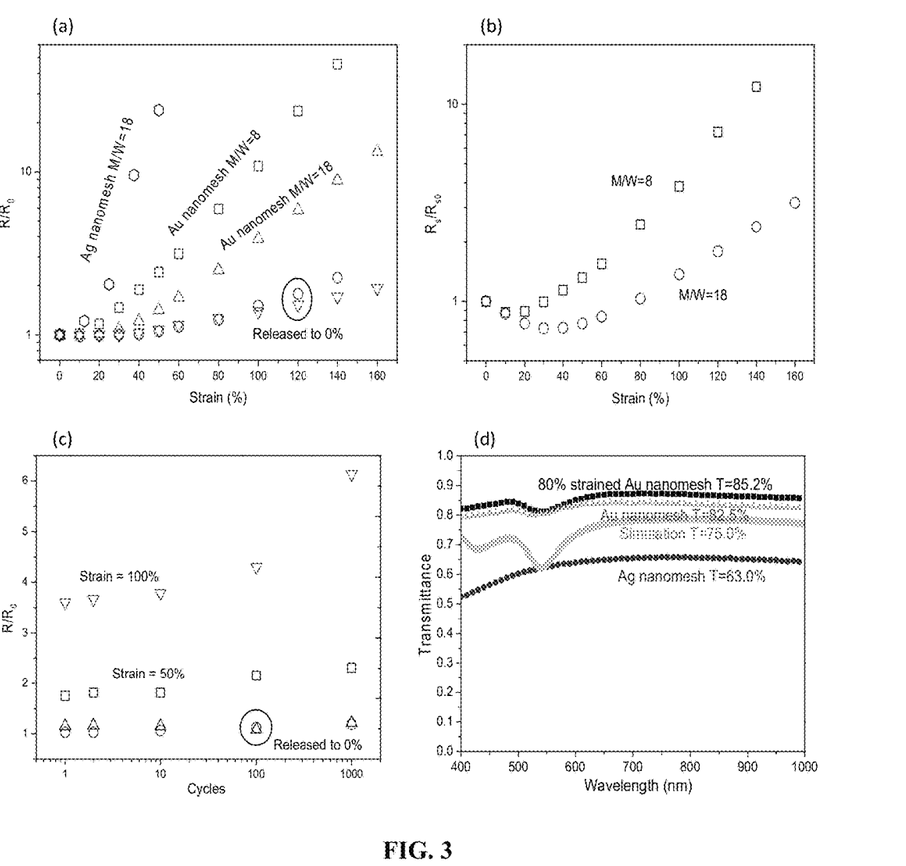
FIG. 3. graphically illustrates (a) the dependence of resistance change ($R/R_0$) on tensile strain, (b) the dependence of sheet resistance ($R_s$) on tensile strain, (c) the resistance change ($R/R_0$) versus cycles and (d) the transmittance in the wavelength range of 400-1000 nm for an exemplary gold nanomesh.

Although the Au nanomesh has a slightly lower electrical conductivity compared to the Ag nanomesh, it is a much better flexible transparent electrode. Au is a metal with excellent ductility, and has demonstrated the desired flexibility of Au nanowires. FIG. 3(a) plots the dependences of resistance change ($R/R_0$, where R and $R_0$ are sheet resistances of stretched and non-stretched nanomeshes, respectively) on tensile strain ($\epsilon$) for Ag and Au nanomeshes supported on PDMS substrate (about 1 mm thick). $R/R_0$ of the Ag nanomesh is quite close to 1 at a strain of 12.5%, but it goes to 24 as $\epsilon$ increases to 50%, and sharply to 870 when $\epsilon$ increases further to 62.5%. This is already too high for many applications. In contrast, $R/R_0$ of the Au nanomesh is only about 3.8 at a strain of 100%, and it increases to 13.3 at an ultra-high strain of 160%, at which the PDMS substrate fractures. This result is even better than that of the Ag nanomesh made of "very long Ag nanowires". The sheet resistance (Rs) of the stretched Au nanomesh, is even smaller than the original sheet resistance ($Rs_0$) until it is stretched to 80% strain or larger. This means the Au nanomesh is even "more conductive" at relatively low strains. And $Rs/R_{s0}$ is only 3.2 as strain goes to 160%. We found that the mesh-size to line width (M/W) ratio could significantly affect the flexibility of the Au nanomeshes. FIGS. 3(a) and (b) shows data of two Au nanomeshes with M/W of 18 and 8, respectively. The sample with larger M/W presents much lower $R/R_0$ and $R_s/R_{s0}$ values (it also has better transmittance of 82.5% but higher sheet resistance of $25\Omega/\square$, compared to 70% transmittance and $15\Omega/\square$ sheet resistance for the sample with a lower M/W). $R/R_0$ returns to a lower value of less than 2 after releasing, probably because of the re-contact and cold welding of fractured nanowire where necking happened. This is evidenced by the fact that it takes time for the release R to drop to the minimum and get stabilized. Au could not be oxidized in air so that no oxide skin will be formed, and this makes cold welding possible. The low released R is significant because it means even when the Au nanomesh is over-stretched, it can still be partially recovered.

The Au nanomesh also shows better transmittance than the Ag nanomesh. FIG. 3(d) plots the transmittance spectra of the Au and Ag nanomesh samples. The Au nanomesh presents a high transmittance of 82.5%, contrasted with 63.0% for the Ag nanomesh (both with a sheet resistance of about $20\Omega/\square$). It should be noted that the data shown here are specular transmittances, or the transmittances emergent from the nanomesh and parallel to the beam entering the nanomesh, and thus do not include scattered transmission portion. For Ag nanomeshes made of solution processed nanowires, scattered transmission is often well more than 10%, that means even the total transmittance achieves 90%, the specular transmission should be lower than 80%. In comparison, dispersed transmission for Au nanomesh is only about 3% (when transmittance exceeds 80%), this may allow its applications in displays or other fields where scattered light is undesired. In addition, we found that the stretched Au nanomesh has a higher transmittance (85.2% at a strain of about 80%). Note that under a strain of 80%, both sheet resistance and transmittance are improved. The higher transmittance of Au nanomesh is related to its low reflectance. A comparison between Au and Ag nanomeshes shows that the reflectance are 5.5% and 14.2%, respectively, measured by an integrating sphere detector. The higher reflectance of the Ag nanomesh is foreseeable because Ag is an excellent reflector that has been widely used for mirrors.

Figure 4:
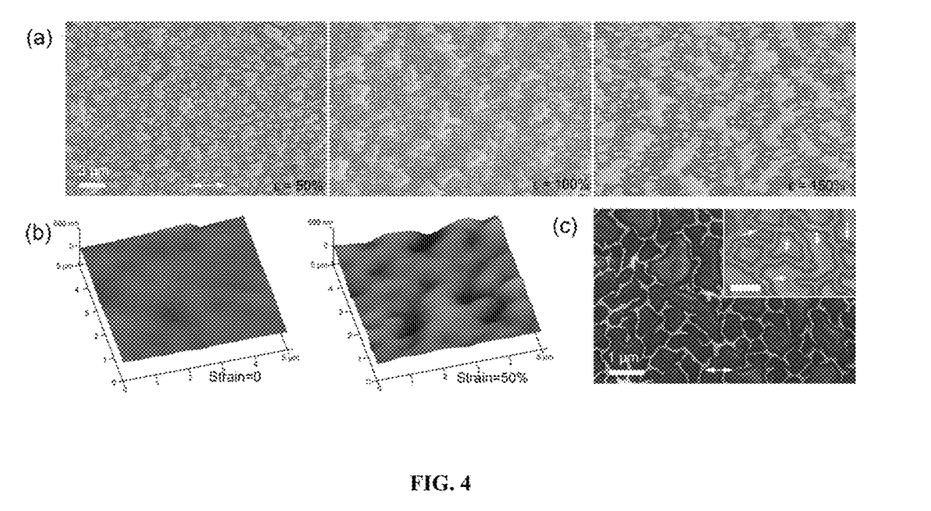
FIG. 4. illustrates (a) a SEM micrographs of the morphology of stretched Au nanomeshes on PDMS substrate with tensile strains of 50%, 100%, and 150%, respectively. (b) atomic force microscopy (AFM) images of non-stretched Au nanomesh, and (f) stretched Au nanomesh with a tensile strain of 50% supported on PDMS according to one embodiment of the present disclosure. (c) a SEM micrographic image of the stretched Au nanomesh showing necking of the Au nanowires.
Figure 6:
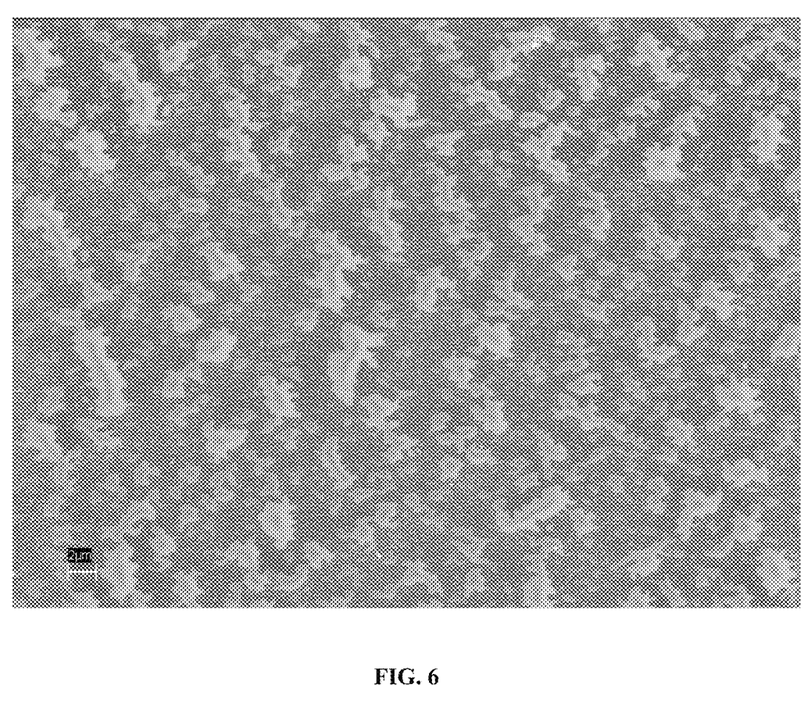
FIG. 6. illustrates an SEM image of stretched Au nanomesh, showing cracks which are formed during stretching. These cracks divide the Au nanomesh into a larger mesh.

The nanomesh could be regarded as randomly woven metallic serpentines. According to some simulations, stretched one dimensional serpentines on a quite soft substrate, could have both in plane and out of plane deformations, which is also experimentally seen in our two dimensional case as in AFM images FIG. 4(b). This shows that further stretching could lead to cracks oriented perpendicularly to the external load, thus forming a hierarchical network as in FIG. 6. The cracks get longer and wider with the increasing of strain, thus resistance gradually increases.

The excellent flexibility and good transmittance of the Au nanomesh makes it very suitable as a transparent electrode for flexible photo-electronic devices. It is better compared to Ag nanomesh in both flexibility and transparency. Moreover, other metal (including Ag and Cu) nanomeshes are prone to be oxidized, leading to a deterioration of electrical and optical properties. For example, solution processed Ag nanomeshes have a dramatic decrease of conductivity annealing at 200° C. or higher for more than 20 min. Cu nanowires are severely oxidized even at room temperature without protection for days. In comparison, Au nanomeshes do not have this oxidation problem and can work at high temperatures up to at least 500° C. In addition, compared to metal nanomeshes made of solution processed metal nanowires, which are quite rough, our metal nanomeshes are more compatible to lithographic process and are possibly used to make microcircuit with a feature size of several microns, which is unavailable by using solution processed Ag nanowire networks.

In conclusion, disclosed are Au nanomeshes fabricated via a non-lithographic bilayer lift-off metallization process, in which the mask layer originates from a self-assembled metallic In film. The nanowire width, mesh size, and thickness of the nanomesh are well tunable. The metal nanomesh supported on silicon substrate can be wedged onto water and further transferred intact to any hydrophobic or hydrophilic substrates. The surface tension of water supports the metal nanomesh on water and also keeps it unfolded. The Au nanomesh presents excellent flexibility ($R/R_0=12.3$ and $R_s/R_{s0}=3.2$ at $\epsilon=160\%$), good specular transmission (82.5%), and quite small dispersed transmittance (about 3%), much better than that of Ag nanomeshes. Also, the Au nanomesh has good thermal stability even heating up to 450° C.

Exemplary embodiments are disclosed herein and variations, combinations, and/or modifications of such embodiment(s) may be made by a person having ordinary skill in the art and are within the scope of the disclosure. Alternative embodiments that result from combining, integrating, and/or omitting features of the expressly-disclosed embodiment(s) are also within the scope of the disclosure. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as "comprises", "includes", and "having" means "including but not limited to" and should be understood to also provide support for narrower terms such as "consisting of", "consisting essentially of", and "comprised substantially of." Accordingly, the scope of protection is not limited by the description set out above but is defined by the claims that follow, that scope including all equivalents of the subject matter of the claims. Each and every claim is incorporated as further disclosure into the specification, and each is an exemplary embodiment of the present invention.

What is claimed is:

1. A metallic nanomesh, comprising:
   a flexible sheet of metallic nanowires comprising palladium (Pd) and at least one conductive elements selected from the group consisting of aluminum (Al), copper (Cu), gold (Au), silver (Ag), platinum (Pt), and the alloys and combinations thereof, wherein the sheet of metallic nanowires comprises randomly woven metallic serpentines;
   wherein the sheet of metallic nanowires is configured to stretch to 200% in at least one dimension at a sheet resistance less than 30 Ω/□; and
   wherein the sheet of nanowires comprises a transmittance of at least about 40% in the spectrum between about 200 nm and about 1500 nm.

2. The metallic nanomesh of claim 1, wherein each nanowire of the sheet of nanowires comprises a thickness between about 10 nm and about 500 nm.

3. The metallic nanomesh of claim 1, wherein each nanowire of the sheet of nanowires comprises a line width between about 20 nm and about 200 nm.

4. The metallic nanomesh of claim 1, wherein the sheet of nanowires comprises a mesh size between about 0.1 μm and about 10 μm.

5. The metallic nanomesh of claim 1, further comprising a strain of at least 200% in at least one direction at a sheet resistance less than 10 Ω/□.

6. A device, comprising:
   a substrate comprising PDMS or a metal; and
   a flexible metallic nanomesh sheet disposed on the substrate and comprising palladium (Pd), wherein the sheet of metallic nanowires comprises randomly woven metallic serpentines, and wherein the sheet of metallic nanowires is configured to stretch to 200% in at least one dimension at a sheet resistance less than 30 Ω/□.

7. The device of claim 6, wherein the nanomesh sheet further comprises at least one additional element selected from the group consisting of: aluminum (Al), copper (Cu), silver (Ag), platinum (Pt), gold (Au) and the alloys and combinations thereof.

8. The device of claim 6, wherein the nanomesh sheet comprises a plurality of nanowires.

9. The device of claim 8, wherein each nanowire of the plurality of nanowires comprises a thickness between about 10 nm and about 500 nm and a line width between about 20 nm and about 200 nm.

10. The device of claim 8, wherein the nanomesh comprises a mesh size between about 0.1 μm and about 10μm.

11. The device of claim 10, wherein the mesh size: line width ratio is at least 8.

12. The device of claim 8, wherein the nanomesh comprises a transmittance of at least about 40% in the spectrum between about 200 nm and about 1500 nm.

* * * * *